United States Patent [19]

Wehrenberg

[11] Patent Number: 4,704,467

[45] Date of Patent: Nov. 3, 1987

[54] METHOD FOR PREPARATION OF MERCAPTOBENZOATES

[75] Inventor: Peter K. Wehrenberg, Oakland, Calif.

[73] Assignee: Stauffer Chemical Company, Westport, Conn.

[21] Appl. No.: 940,995

[22] Filed: Dec. 12, 1986

[51] Int. Cl.⁴ .................. C07C 149/40; C07C 147/14; C07C 147/107

[52] U.S. Cl. ........................ 560/11; 560/12; 560/18

[58] Field of Search ............................. 560/11, 12, 18

[56] References Cited

U.S. PATENT DOCUMENTS 3,663,615  5/1972  Ziegler ................................. 564/80
3,729,508  4/1973  Ziegler ................................. 560/18
3,867,433  2/1975  Shen .................................. 562/427

OTHER PUBLICATIONS

Cogolli, J. Org. Chem., 44, pp. 2636–2642 (1979).

Primary Examiner—Michael L. Shippen
Attorney, Agent, or Firm—Joel G. Ackerman

[57] ABSTRACT

A method of preparing a compound of the formula

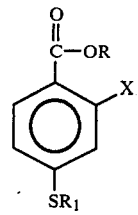

wherein R is alkyl, $R_1$ is alkyl or aryl and X is halogen or nitro comprising reacting

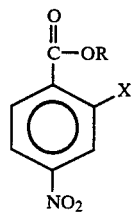

wherein R and X are as defined above with a mercaptan having the formula R-SH in the presence of an inorganic base, a phase transfer catalyst and a non-polar aprotic solvent.

32 Claims, No Drawings

METHOD FOR PREPARATION OF MERCAPTOBENZOATES

BACKGROUND OF THE INVENTION

Compounds of the type

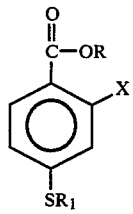

wherein R is alkyl, $R_1$ is alkyl, alkenyl, aryl or benzyl and X is halogen or nitro, are useful intermediates in the synthesis of pesticides, such as herbicides whose structures include alkylthio and alkylsulfonyl benzoates. These intermediates have been produced by various methods, including a two-step procedure, as described in the accompanying patent application of Charles G. Carter et al., entitled "Method for Preparation of Mercaptobenzoates" Ser. No. 940,977, commonly assigned and concurrently filed herewith, in which, in the first step, a nitrobenzoate is reacted with a mercaptan in the presence of a base, to give a mercaptobenzoate and in the second, the mercapto group is oxidized to a sulfoxide or sulfone. The first step of this process requires a polar aprotic solvent such as acetone or methyl isobutyl ketone which is subject to reaction with oxidants such as sodium hypochlorite used in the oxidation step. One skilled in the art would recognize the usefulness of utilizing the same solvent in both steps of the reaction.

SUMMARY OF THE INVENTION

When a phase transfer catalyst is used in the first step, a non-polar aprotic solvent may be used. This same solvent is also useful in the oxidation step, thus the need for a change of solvent or isolation of the intermediate between steps is avoided. Optionally, the solution of intermediate mercaptobenzoate may be washed with water to remove undesired salts and then oxidized without isolation of the intermediate.

DESCRIPTION OF THE INVENTION

According to this invention, compounds of the formula

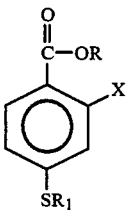

wherein R, $R_1$ and X are as defined can be prepared by reacting a compound of the formula

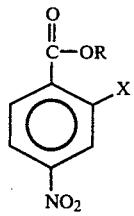

with a mercaptan having the formula R—SH in the presence of an inorganic base in a non-polar aprotic solvent which is inert to nucleophilic addition. A catalyst amount of a phase transfer catalyst promotes formation of a soluble nucleophile and allows displacement of the 4-nitro group with a mercapto group.

Mercaptans which are useful in this reaction can be selected from alkyl, alkenyl, aryl or benzyl mercaptans. The term "alkyl" includes both straight and branched chain saturated acylic hydrocarbyl moieties and generally includes moieties having from 1 to 8 carbon atoms, preferably from 1 to 3. The term "alkenyl" includes both straight and branched chain unsaturated acyclic hydrocarbyl moieties and generally includes moieties having from 2 to 8 carbon atoms, preferably from 2 to 3. The term "aryl" includes phenyl and substituted phenyl. The inorganic bases which can be used include potassium carbonate, sodium carbonate, tripotassium phosphate and trisodium phosphate. Non-polar aprotic solvents which can be used include hydrocarbons such as benzene, toluene, xylenes; halogenated hydrocarbons such as dichloromethane, 1,2-dichloroethane, chlorobenzene; ethers such as tetrahydrofuran, diethyl ether, diisobutyl ether and other organic solvents. Phase transfer catalysts which can be used include tris-(3,7-dioxahepty)amine (TDA-1), tricaprylylmethylammonium chloride (Aliquat 336 ®), tetra-lower alkyl substituted ammonium, phosphonium, sulfonium and sulfoxonium halides, crown ethers and criptates.

The reaction is preferably run at a temperature from about 0° to about 200° C., more preferably from about 25° to about 100° C., most preferably from about 40° to about 60° C. This reaction can be run at atmospheric, sub-atmospheric or super-atmospheric pressure, preferably at atmospheric pressure. The phase transfer catalyst can be present in from about 0.5 to about 100 mole %, preferably from about 1.0 to about 20 mole %, most preferably from about 3 to about 10 mole %. Preferred bases are potassium carbonate and sodium carbonate, most preferably potassium carbonate. Preferred solvents are hydrocarbons and halogenated hydrocarbons, more preferably halogenated hydrocarbons, most preferably chlorinated hydrocarbons such as 1,2-dichloroethane.

When performing a 2-step reaction as in the present invention, the solvent must be compatible in each step. 1,2-Dichloroethane, although the solvent of choice of the present invention, is only one of many solvents which are suitable. It is a useful solvent in forming the mercaptobenzoate and is not subject to reaction with oxidants such as sodium hypochlorite in the oxidation reaction.

The process of this invention can be better understood by reference to the following examples. Examples 1 and 3 illustrate methods for the preparation of the mercaptobenzoate. Example 2 serves to confirm the structure of Example 1 through analysis of the resulting sulfonyl benzoic acid and also serves to illustrate the use of the solvent of choice of Example 1 in the oxidation step. The product of Example 1 need not be isolated, but can be further reacted before or after removal of the salts formed in Example 1. If desired, solvent can be added or removed to achieve the desired volume in the oxidation step.

EXAMPLE 1

Preparation of Methyl 2-Chloro-4-methylthiobenzoate

To a multineck round bottom flask equipped with a dry ice condenser and a septum with a gas inlet were added methyl 2-chloro-4-nitrobenzoate (4.3 grams g, 0.02 moles), 40 milliliters (ml) 1,2-dichloroethane, 3.9 g potassium carbonate (0.028 m) and 0.3 g (0.001 m) TDA-1. The mixture was heated to 50° C. Methyl mercaptan was introduced in an above-surface addition until the mercaptan refluxed in the dry ice condenser. After approximately 20 minutes of reflux, high pressure liquid chromatography (HPLC) showed 92.5% of product present in the mixture.

The reaction mixture was treated with 40 ml water followed by 20 ml 1N hydrochloric acid (HCl) and the organic phase evaporated under reduced pressure to yield 4.3 g of the benzoate with 96.8 area % of the desired material shown by high pressure liquid chromatography (HPLC).

EXAMPLE 2

Preparation of 2-Chloro-4-methanesulfonyl benzoic acid

To a single neck, round-bottom flask were added 4.3 g (0.02 m) methyl 2-chloro-4-methylthiobenzoate produced in Example I and 60 ml 1,2-dichloroethane. Sodium hypochlorite, 85 g (0.06 m, 5.25% in water) was added dropwise and the exothermic reaction was allowed to heat. When the addition was complete, the mixture was heated to 60° C. over 1.5 hours then allowed to stir overnight at ambient temperature. The excess sodium hypochlorite was decomposed with 4.5 g (0.075 mole) sodium bisulfite. 6.4 g (0.16 mole) 50% sodium hydroxide (NaOH) were added to the mixture which was then heated to 60° C. over 2 hours. The mixture was cooled to ambient temperature and extracted with 2×12 ml 1,2-dichloroethane (EDC). The EDC was extracted with 25 ml water and the pH of the aqueous phase was adjusted to 14 with 50% NaOH. Aqueous phases were combined and acidified to pH 0-1 with 18% hydrochloric acid and the resulting solids filtered off to yield 3.93 g of product with a melting point of 187°–192° C. HPLC determined the sulfone to be 94.9 weight percent of the benzoic acid with a technical yield of 91.4%.

EXAMPLE 3

Preparation of Methyl 2-Chloro-4-methylthiobenzoate

To a multi-neck round bottom flask equipped as in Example I were added 21.6 g (0.1 m) methyl 2-chloro-4-nitrobenzoate, 125 ml 1,2-dichloroethane, 27.6 g (0.2 m) potassium carbonate, and 2.0 g (0.005 m) Aliquat ® 336. The mixture was heated to 60° C. 14.4 g (0.3 m) methyl mercaptan were introduced in an above-surface addition over a period of 6 minutes. The mixture was allowed to stir while heating at 58° C. for 12 hours. The temperature was then increased to 70° C. and the reaction allowed to stir another 7 hours.

HPLC showed the reaction mixture to contain 74.2% of the desired product.

What is claimed is:

1. A method of preparing a compound having the formula

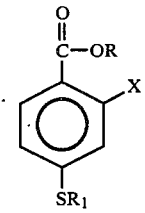

wherein R is alkyl; $R_1$ is alkyl, alkenyl, aryl or benzyl; and X is halogen or nitro comprising reacting a benzoate of the formula

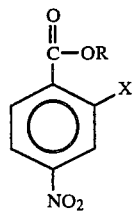

wherein R and X are as defined with a mercaptan of the formula $R_1$—SH wherein $R_1$ is as defined in the presence of a non-polar aprotic solvent, an inorganic base and a phase transfer catalyst.

2. A method according to claim 1 wherein R and $R_1$ are each $C_1$–$C_8$ alkyl and X is halogen.

3. A method according to claim 1 wherein R and $R_1$ are each $C_1$–$C_3$ alkyl and X is chlorine.

4. A method according to claim 1 wherein R and $R_1$ are both methyl and X is chlorine.

5. A method according to claim 1 wherein the temperature is from about 25° to about 100° C.

6. A method according to claim 1 wherein the temperature is from about 40° to about 60° C.

7. A method according to claim 1 wherein the catalyst is tris-(3,7-dioxaheptyl)amine.

8. A method according to claim 1 wherein the catalyst is tricaprylylmethylammonium chloride.

9. A method according to claim 1 wherein the solvent is a hydrocarbon.

10. A method according to claim 1 wherein the solvent is a halogenated hydrocarbon.

11. A method according to claim 1 wherein the solvent is a chlorinated hydrocarbon.

12. A method according to claim 1 wherein the solvent is 1,2-dichloroethane.

13. A method according to claim 1 wherein the base is a phosphate.

14. A method according to claim 1 wherein the base is a carbonate.

15. A method according to claim 1 wherein the base is potassium carbonate.

16. A method of preparing a compound having the formula

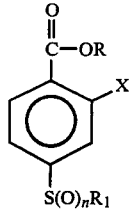

wherein R is alkyl; $R_1$ is alkyl, alkenyl, aryl or benzyl; X is halogen or nitro; and n is 1 or 2 comprising (a) reacting a nitrobenzoate of the formula

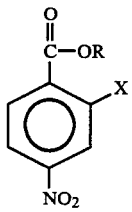

wherein R and X are as defined with a mercaptan of the formula $R_1$—SH wherein $R_1$ is as defined to produce a mercaptobenzoate of the formula

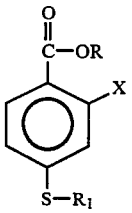

in the presence of a non-polar aprotic solvent, an inorganic base and a phase transfer catalyst; and (b) oxidizing the mercaptobenzoate formed in step (a) in the presence of a non-polar aprotic solvent of step (a).

17. A method according to claim 16 wherein the solvent of step (a) is retained in the reaction of step (b).

18. A method according to claim 16 wherein the mercaptobenzoate formed in step (a) is isolated and then oxidized in the presence of a non-polar aprotic solvent of choice of step (a).

19. A method according to step (a) of claim 16 wherein R and $R_1$ are each $C_1$-$C_8$ alkyl and X is halogen.

20. A method according to step (a) of claim 16 wherein R and $R_1$ are each $C_1$-$C_3$ alkyl and X is chlorine.

21. A method according to step (a) of claim 16 wherein R and $R_1$ are both methyl and X is chlorine.

22. A method according to step (a) of claim 16 wherein the temperature is from about 25° to about 100° C.

23. A method according to step (a) of claim 16 wherein the temperature is from about 40° to about 60° C.

24. A method according to step (a) of claim 16 wherein the catalyst is tris(3,7-dioxaheptyl)amine.

25. A method according to step (a) of claim 16 wherein the catalyst is tricaprylylmethylammonium chloride.

26. A method according to step (a) of claim 16 wherein the solvent is a hydrocarbon.

27. A method according to step (a) of claim 16 wherein the solvent is a halogenated hydrocarbon.

28. A method according to step (a) of claim 16 wherein the solvent is a chlorinated hydrocarbon.

29. A method according to step (a) of claim 16 wherein the solvent is 1,2-dichloroethane.

30. A method according to step (a) of claim 16 wherein the base is a phosphate.

31. A method according to step (a) of claim 16 wherein the base is a carbonate.

32. A method according to step (a) of claim 16 wherein the base is potassium carbonate.

* * * * *